(12) United States Patent
Foulquier et al.

(10) Patent No.: US 7,397,024 B2
(45) Date of Patent: Jul. 8, 2008

(54) PHANTOM FOR THE QUALITY CONTROL OF A RADIOTHERAPY TREATMENT VIRTUAL SIMULATION SYSTEM

(75) Inventors: Jean-Noël Foulquier, Nogent sur Marne (FR); Hanna El-Balaa, Vitry sur Seine (FR); Dimitri Lefkopoulos, Nemours (FR)

(73) Assignee: Assistance Publique - Hopitaux de Paris, Paris (FR)

( * ) Notice: Subject to any disclaimer, the term of this patent is extended or adjusted under 35 U.S.C. 154(b) by 270 days.

(21) Appl. No.: 10/553,781

(22) PCT Filed: Apr. 22, 2004

(86) PCT No.: PCT/FR2004/000987

§ 371 (c)(1),
(2), (4) Date: Apr. 14, 2006

(87) PCT Pub. No.: WO2004/096047

PCT Pub. Date: Nov. 11, 2004

(65) Prior Publication Data

US 2006/0239414 A1    Oct. 26, 2006

(30) Foreign Application Priority Data

Apr. 23, 2003  (FR)  .................... 03 04987

(51) Int. Cl.
*G01D 18/00* (2006.01)
(52) U.S. Cl. .................... 250/252.1; 378/207; 378/18
(58) Field of Classification Search .............. 250/252.1; 378/207, 18
See application file for complete search history.

(56) References Cited

U.S. PATENT DOCUMENTS

| | | | |
|---|---|---|---|
| 4,055,771 A | | 10/1977 | Goodenough et al. |
| 4,352,020 A | * | 9/1982 | Horiba et al. .................. 378/18 |
| 4,613,754 A | * | 9/1986 | Vinegar et al. ........... 250/252.1 |
| 4,646,334 A | * | 2/1987 | Zerhouni ..................... 378/18 |

(Continued)

FOREIGN PATENT DOCUMENTS

DE    198 19 928    11/1999

*Primary Examiner*—Christine Sung
(74) *Attorney, Agent, or Firm*—Jacobson Holman PLLC

(57) ABSTRACT

The invention relates to a phantom for the quality control of a radiotherapy treatment virtual simulation system which comprises a medical imaging device, characterized in that it comprises:
  a support casing (1),
  a core (4) which is arranged in the support casing (1) and which is constituted by a plurality of elements (5, 6, 7, 8, 11, 12, 14, 15, 16, 17) of different shapes, dimensions and densities, the densities simulating the densities of various organs and media of the human body, two of these elements (11, 12) being constituted by two truncated pyramids of different densities which are fitted one inside the other, at least one of them not being completely symmetrical relative to the longitudinal axis thereof,
  balls (9, 10, 13) of a non-radiotransparent material arranged in the core (4),
  at least two removable lateral faces (18, 21) which face each other and which comprise metal wires which define geometric figures.

4 Claims, 2 Drawing Sheets

U.S. PATENT DOCUMENTS

| | | | |
|---|---|---|---|
| 4,873,707 A * | 10/1989 | Robertson | 378/18 |
| 4,985,906 A * | 1/1991 | Arnold | 378/18 |
| 5,416,816 A * | 5/1995 | Wenstrup et al. | 378/18 |
| 6,231,231 B1 * | 5/2001 | Farrokhnia et al. | 378/207 |
| 6,409,515 B1 | 6/2002 | Persohn et al. | |
| 6,674,834 B1 * | 1/2004 | Acharya et al. | 378/18 |
| 7,127,096 B2 * | 10/2006 | Kaufman et al. | 382/131 |
| 2003/0048867 A1 * | 3/2003 | Acharya et al. | 378/18 |
| 2007/0189453 A1 * | 8/2007 | Yang et al. | 378/56 |

* cited by examiner

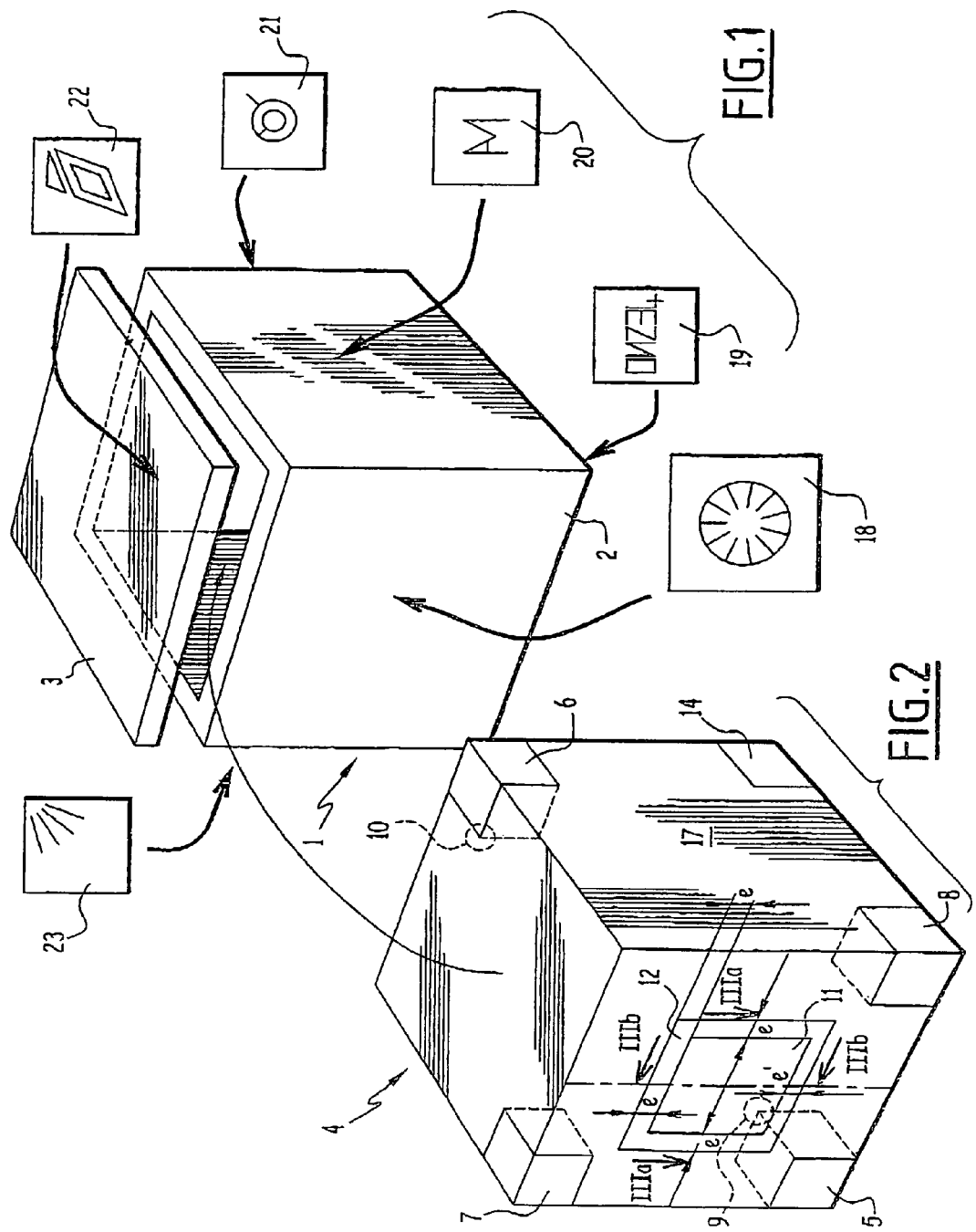

PHANTOM FOR THE QUALITY CONTROL OF A RADIOTHERAPY TREATMENT VIRTUAL SIMULATION SYSTEM

This is a 371 of PCT/FR04/000987 filed Apr. 22, 2004.

The present invention relates to the field of radiotherapy. More precisely, it relates to a device of the type referred to as a "phantom" which is used for the preparation of equipment during virtual simulation operations for preparing to carry out radiotherapy treatment using a scanner or the like.

The treatment of tumours using radiotherapy is nowadays possible using equipment which comprises a medical imaging device, such as a scanner, coupled to a device for emitting the radiation used to treat the patient. The preparation of this equipment, before the irradiation of the patient is effectively carried out, comprises a step referred to as "virtual simulation".

This term refers to an assembly of pieces of software which allows the user to define or calculate what is referred to as the "treatment isocentre", that is to say, the localised zone in which the radiation which is to destroy the tumour must converge, then to simulate the treatment to be carried out using reconstructed radiological plates. Two software components are used during the virtual simulation phase:

- pieces of software which define the contours, on the one hand, of the tumour to be treated and, on the other hand, of the organs which it is important not to affect when the radiation is emitted;
- and pieces of software which allow the beams to be positioned owing to the examination of the reconstructed radiographs and allows the covers or the blades of the collimator to be positioned.

The device which brings about the virtual simulation proposes all the movements of a particle accelerator using configured software. However, the relevance of the data provided by this software can conventionally be verified only during a simulation operation which is carried out with the patient present, which is restrictive for the patient. It is therefore desirable to have a tool which would allow the relevance of the operation of the virtual simulation software to be verified without the patient being present.

It is known to use, for the calibration of scanners, devices known as "phantoms". They are constituted by a volume of known dimensions of a material (water, polystyrene of various densities, plexiglass) which behaves substantially in the same manner as the human tissue which is to be examined, in terms of the absorption and diffusion of the radiation used. These known phantoms are not suitable for carrying out a virtual simulation as defined above.

It has been proposed in the document "A quality assurance phantom for digitally reconstructed radiograph (DRRs) Med Phys 1994. 21, 902", that a phantom be used which is constituted by a polystyrene frame having a side 15 cm long and which comprises four test faces. It allows an evaluation of the spatial resolution of the device to be carried out. Geometric shapes are engraved on the main face and allow the measurement of the modulation transfer function, the degree of contrast, the spatial linearity of the reconstructed radiographs and the quality of the algorithm for reconstructing the reconstructed radiographs for a divergent beam. However, this phantom does not allow all the operations to be carried out which are required in order to verify the quality of the virtual simulation. It is therefore always necessary, in order to verify the overall quality of a virtual simulation, to carry out a plurality of successive analyses of different test objects, which requires the scanner and the virtual simulation console to be kept available for a considerable length of time.

The object of the invention is to provide a phantom which allows all the virtual simulation functions of a radiotherapy system which uses an imaging device, such as a scanner, to be tested during a minimal number of operations.

To this end, the invention relates to a phantom for the quality control of a radiotherapy treatment virtual simulation system which comprises a medical imaging device, characterised in that it comprises:

- a support casing,
- a core which is arranged in the support casing and which is constituted by a plurality of elements of different shapes, dimensions and densities, the densities simulating the densities of various organs and media of the human body, two of these elements being constituted by two truncated pyramids of different densities which are fitted one inside the other, at least one of them not being completely symmetrical relative to the longitudinal axis thereof,
- balls of a non-radiotransparent material arranged in the core,
- at least two removable lateral faces which are opposite to each other and which comprise metal wires which define geometric figures.

The phantom is preferably generally of cubic form.

One of the balls is preferably placed at the centre of the core.

The phantom preferably comprises six removable lateral faces which comprise metal wires which define geometric figures.

As will be appreciated, the phantom according to the invention is composed first of all of a support casing, preferably of cubic form. At least two plates are mounted on this support casing, on which plates a geometric figure is marked out using metal wires which are embedded at that location, and which are placed opposite each other on the support casing. These two plates are used to verify that the divergence of the reconstructed image is correct.

Advantageously, all the faces of the support casing comprise plates of this type so that it is possible to carry out a maximum number of divergence tests during a single operation. The casing is provided, at the inner side, with volumes which have notable geometric shapes and different densities which allow the densities of various organs (such as the breast, muscles, bones, lungs filled with air) to be simulated. One of these volumes in particular is constituted by fitted truncated pyramids. A specific number of metal balls, preferably steel balls, are placed inside these volumes at defined positions. One of these balls is preferably placed at the centre of the phantom. These balls constitute reference points for treatment isocentres. Comparison of the image of the volumes with which the casing is provided and reality allows the correct calibration of the virtual simulation software to be verified.

The invention will be better understood from a reading of the following description, given with reference to the appended drawings, in which:

FIG. 1 is a perspective view of an example of a support casing for a phantom according to the invention and the lateral faces which are associated therewith;

FIG. 2 is a perspective view of an example of a core which is intended to be inserted in the support casing;

Figure 3A:
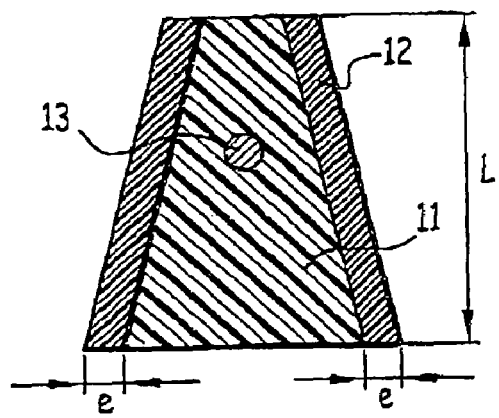
FIG. 3 is a sectioned view along III-III (FIG. 3a) and along IV-IV (FIG. 3b) of a portion of the core.
Figure 3B:
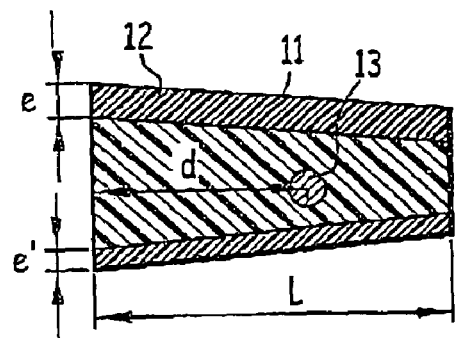
Figure 4:
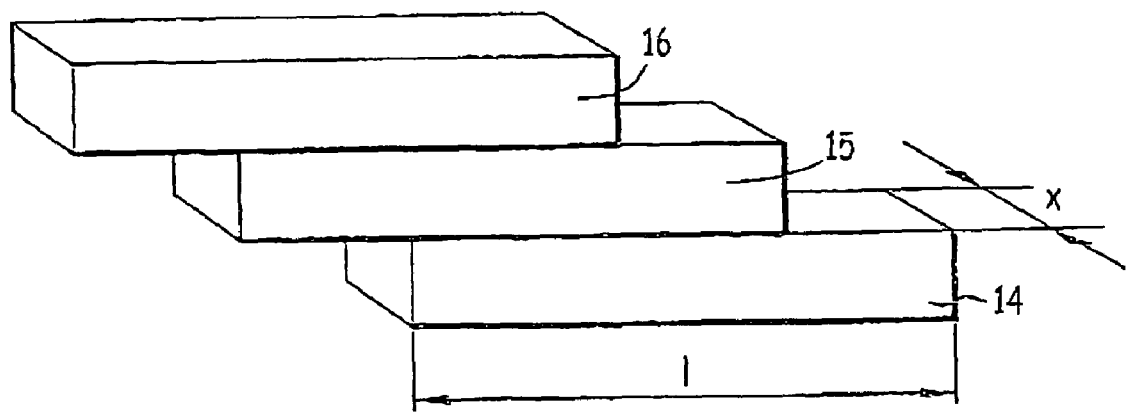
FIG. 4 is a perspective view of another portion of the core.

The support casing 1 which is illustrated in FIG. 1 is constituted by the assembly of two elements which, in the example illustrated, constitute a cube having sides 19 cm long. The first element 2 is a case which is open at the upper face thereof and whose base is a square which has sides 19 cm long and whose lateral faces are 18 cm tall. The second element 3 is a square plate which has sides 19 cm long and a thickness of 1 cm and which is arranged at the upper portion of the casing 1 so as to form a cover for the first element 2. These two elements 2, 3 are of a material such as high-impact polystyrene (having a density of 1.05) but could also be of polymethylmethacrylate (PMMA), for example. These two elements 2, 3 are fixedly joined by means of screws of a material such as nylon, having a length of 2 cm.

The support casing 2 is intended to comprise a core 4, one example of which is illustrated in FIG. 2.

This core 4 is constituted by a cubic assembly which has sides 17 cm long and which is composed of elements, some of which have notable geometric properties, and having different densities which represent the densities of the various organs and media of the human body which the radiation of the radiotherapy device may pass through. These elements include four cubes 5, 6, 7, 8 which have sides 3.5 cm long and which each occupy an apex of the core 4. Two of these cubes 5, 6 are placed on two diagonally opposed apices. These cubes 5, 6, 7, 8 all have different densities. For example, cube 5 has a density of 0.991 which simulates that of the breast, cube 6 has a density of 1.609 which simulates that of bone, cube 7 has a density of 1.062 which simulates that of muscle and cube 8 has a density of 0.465 which simulates that of the lung in the exhaled state. There are placed, at the apices of the cubes 5, 6 located at the points having the co-ordinates (5;5;5) and (−5; −5, −5), in the reference frame which has the centre of the core 4 as the origin, balls 9, 10 of a non-radiotransparent material, such as steel, which are intended to simulate treatment isocentres. Steel is selected in preference to other materials since it can be clearly seen in the reconstructed images and does not bring about too many artefacts in the image.

Other elements are constituted by an element 11 in the form of a truncated pyramid which has a length "L"=13.5 cm and whose large base is a square having sides which are 5.5 cm long, and by an element 12 which covers the element 11 and which has an outer shape which is not completely symmetrical relative to the longitudinal axis thereof. It surrounds the element 11 over a thickness "e'"=1 cm along three of the sides of the large base thereof and over a thickness "e"=0.5 cm along the fourth side. These two elements 11, 12 have different densities. The assembly formed by these two elements 11, 12 is intended to form the central portion of the core 4. It has a length "L" of 13.5 cm, therefore less than the length of an edge of the core 4 through which it does not therefore extend from end to end. Preferably, at the centre of the element 11, at a distance "d" from the large base of 8.5 cm, there is located a steel ball 13 which simulates a treatment isocentre. The distance "d" is selected so that the ball 13 is located exactly at the centre of the cube formed by the assembled core 4.

In the portion of the core 4 that is located set back from the truncated pyramid-like elements 11, 12, three parallelepipedal elements 14, 15, 16 are also integrated and have a length "l"=6 cm and a width and thickness of 2 cm. These elements are arranged so as to be superimposed and offset longitudinally relative to each other. Once again, they each have different densities which simulate various constituents of the human body.

The remainder 17 of the cubic core 4 in which the various elements 5, 6, 7, 8, 11, 12, 14, 15, 16 are placed is constituted by a polystyrene member.

Finally, the casing 1 is covered over the six faces thereof by square plates 18, 19, 20, 21, 22, 23 which have sides which are 20 cm long and a thickness of 0.5 cm and which are fixed thereto in a removable manner by means of screws which are 1 cm long and which are of a radiotransparent material, such as nylon. These plates 18-23 are of plexiglass and comprise, embedded in the mass thereof, wires of a metal such as copper which form geometric figures such as those illustrated in FIG. 1. Each of those figures can be dedicated to the verification of one or more specific functions of the software, in view of the manner in which the software has reconstituted their shape. Having six removable plates 18-23 of this type is advantageous in that it allows a maximum number of functions to be tested during a single trial. It would remain within the scope of the invention to provide a smaller number of removable plates. However, a minimum of two plates 18-23 arranged on two opposing faces of the core 4 is required to verify that the divergence of the reconstructed image is correct. To this end, patterns which form circles as illustrated on the plates 18, 21 in FIG. 1 are particularly recommended.

The phantom which has been described and illustrated above is only one example; in particular, it would remain within the scope of the invention to confer on the phantom a shape other than that of a cube. The cube has the advantage that it can be readily manipulated and the plates 18-23 which constitute the outer faces thereof can be interchanged. The shapes and the dimensions of the elements which form the core 4 can be different from those which have been described. However, the presence of fitted elements 11, 12 in the form of truncated pyramids having different densities is essential.

This allows the verification of:
  the capacity of the software to carry out in a precise manner automatic contouring operations for organs of different densities;
  the precision of the safety margins which can be allocated to an organ which will move during treatment; the fact that the element 12 is asymmetrical is desirable in order to verify a non-symmetrical organ expansion; knowing the thicknesses of the elements 11 and 12, it is possible to compare the measurement of these elements with the calculation of the margin made by the software which must correspond to the thickness of the material of the outer element 12;
  the capacity of the software to interpolate different contours; it is thus possible to estimate the precision of the reconstruction of the volume.

The invention claimed is:

1. Phantom for the quality control of a radiotherapy treatment virtual simulation system which comprises a medical imaging device, characterised in that it comprises:
    a support casing (1),
    a core (4) which is arranged in the support casing (1) and which is constituted by a plurality of elements (5, 6, 7, 8, 11, 12, 14, 15, 16, 17) of different shapes, dimensions and densities, the densities simulating the densities of various organs and media of the human body, two of these elements (11, 12) being constituted by two truncated pyramids of different densities which are fitted one inside the other, at least one of them not being completely symmetrical relative to the longitudinal axis thereof, balls (9, 10, 13) of a non-radiotransparent material arranged in the core (4), at least two removable lateral faces (18, 21) which face each other and which comprise metal wires which define geometric figures.

2. Phantom according to claim 1, characterized in that it is generally of cubic form.

3. Phantom according to claim 1, characterized in that one of the balls (13) is placed at the centre of the core (4).

4. Phantom according to claim 1, characterized in that it comprises six removable lateral faces (18-23) which comprise metal wires which define geometric figures.

* * * * *